United States Patent [19]
Lemke

[11] Patent Number: 5,978,161
[45] Date of Patent: Nov. 2, 1999

[54] MAGNETIC DEVICE FOR FOCUSING AN OPTICAL IMAGING SYSTEM

[75] Inventor: Norbert Lemke, Dansiger Str. 21, D-82194, Gröbenzelle, Germany

[73] Assignees: Norbert Lemke; Rosemarie Lemke, both of Grobenzell, Germany

[21] Appl. No.: 08/862,254

[22] Filed: May 23, 1997

[30] Foreign Application Priority Data

May 23, 1996 [DE] Germany .......................... 196 20 854
Dec. 6, 1996 [DE] Germany .......................... 196 50 711

[51] Int. Cl.[6] ..................................................... G02B 7/02
[52] U.S. Cl. ............................................................. 359/824
[58] Field of Search .................................. 359/694, 814, 359/822, 824, 704

[56] References Cited

U.S. PATENT DOCUMENTS

5,691,842  11/1997  Devenyi et al. ..................... 359/432

*Primary Examiner*—Georgia Epps
*Assistant Examiner*—Ricky Mack
*Attorney, Agent, or Firm*—Antonelli, Terry, Stout & Kraus, LLP

[57] ABSTRACT

A device for changing the position of an optical imaging system. In one preferred embodiment, a supporting ring surrounds the optical imaging system at least partially. At least one unit is provided which generates or is sensitive to a magnetic field. A casing element surrounds the supporting ring in a largely non-contacting manner, which provides a watertight enclosure of the supporting ring, inclusive of the optical imaging system. A controller surrounds the casing element, at least partially, and is provided with an equal number of units generating or sensitive to a magnetic field in a radial or axial direction relative to the unit in the supporting ring. The controller unit permits a non-contacting displacement of the supporting ring, inclusive of the optical imaging system, along the direction of its optical axis without any wear-inducing engaging operative mechanisms, by means of a magnetic force. In a second embodiment, the controller is a rod-shaped magnetic carrier.

23 Claims, 6 Drawing Sheets

MAGNETIC DEVICE FOR FOCUSING AN OPTICAL IMAGING SYSTEM

BACKGROUND OF THE INVENTION

The present invention relates to a device for changing the position of an optical imaging system. Such optical imaging systems are preferably disposed between an object, e.g. a visual display endoscope, and a camera unit.

The application of video cameras in biomedical engineering, which are employed particularly in combination with endoscopes for observing intracorporeal regions, has been known for quite a time. The video technology introduced in biomedical engineering permits the display of minute intracorporeal regions on a monitor and hence allows for an enlarged display of the region to be treated for observation. Additionally it provides an opportunity for several persons to follow up a surgical operation, at least visually. Compliance with the high demands in terms of sterilization, which are common in surgery, requires a maximum of sterilization of the instruments used in a video-assisted endoscopic surgical operation, However, this is a requirement which neither of interest in common recording and video engineering nor has so far been considered in the design and implementation of such equipment. The "endoscope video systems" employed in biomedical engineering are composed of an observation endoscope which is connected by means of a coupler, e.g. of the type described in the German Patent 37 10 648 C2, via an optical imaging system to a video camera unit. The demands on sterilization of the common endoscopes and, on account of their technological designs, the video cameras currently on the market comply with today's medical standards which require easy sterilizability.

The optical imaging systems so far employed, which serve to focus the intracorporeal regions under observation by means of a visual endoscope sharply onto the imaging plane located in the video camera, include mechanical adjusting mechanisms which permit a displacement of the optical imaging system along the optical axis. Such adjusting mechanisms generally consist of a small focusing lever provided on the outer wall of a casing which accommodates the optical imaging system. Appropriately engaging and intermeshing gears or worm gear threads may be provided for the axial adjustment of the optical imaging system, which is arranged inside the casing, by tilting the outside focusing lever for adjustment inside the casing. This requires, however, at least one drive shaft extending through the casing wall. For compliance with the requirement of sterile conditions it is necessary to ensure appropriate sealing provisions so as to prevent any liquid from penetrating into the interior space of the casing which houses the optical imaging system. To this end the penetrating ducts must be provided with suitable seals in particular, through which passes the connecting shaft between the focusing lever and an adjusting mechanism for adjustment of the position of the optical imaging system.

Apart from expensive and complex sealing provisions, which are indispensable in the known adjusting mechanisms for focusing of the optical imaging system, there is the further disadvantage of wear of these seals, which are subject to a permanent removal of material due to friction caused by the focusing movement so that such sealing provisions need maintenance and replacement after a certain time.

Another disadvantage of the known adjusting mechanisms for changing the position of the optical imaging system, which may also consist of a solid housing element and an adjusting ring for instance e.g. of the type common from the field of photographic lenses, resides in their poor operating and handling characteristics, as with such adjusting mechanisms a single-handed operation is extremely troublesome, if not entirely impossible, and demands a great deal of adaptation and habituation. Moreover the known adjusting mechanisms do not provide any symmetry for left-handed and right-handed operation.

SUMMARY OF THE INVENTION

The present invention is based on the object of improving a device for changing the position of an optical imaging system, which is preferably adapted for being mounted between a visual endoscope or an object to be imaged or virtually represents an object to be imaged, on the one hand, and a camera unit, on the other hand, in a way that an easy single-handed operation will be possible for both left-handed and right-handed persons. In particular, the adjusting mechanism of the optical imaging system should be so configured that it may be easily sterilized and satisfies any current requirements in biomedical engineering. In particular, in the structure of such a device any parts subject to wear should be omitted so that one can dispense with seals subject to wear. Apart therefrom, the overall dimensions should not exceed the sizes of devices, in particular, which have so far been common for changing the position of such imaging systems.

The present invention is based on the idea of providing an optical imaging system, which is preferably adapted for being mounted between an object to be imaged or an optical endoscope for visual observation and a camera unit, with a drive system operating on the principle of magnetic transmission of forces so, that the system can be spatially manipulated in this way. With such a layout the optical imaging system is particularly surrounded by a casing element in a watertight manner, which casing is designed for detachable fastening, e.g. on a camera unit.

In accordance with the present invention, the optical imaging system is surrounded, at least in part, by a supporting ring in which at least one unit is provided which generates or is sensitive to a magnetic field. The supporting ring as such is surrounded by the aforementioned casing element, in a largely non-contacting manner, which casing element ensures a watertight enclosure of the supporting ring inclusive of the optical imaging system. The casing element in its turn is surrounded, at least in part, by a controller which provides equally for at least one unit generating or sensitive to a magnetic field in a radial and/or axial direction relative to the unit in the supporting ring, which generates or is sensitive to a magnetic field, so that the magnetic interaction of the opposing units which generate or are sensitive to a magnetic field insures a transmission of rotating or axial movements by the controller to the inner supporting ring. In this manner any penetrating ducts can be omitted, which would serve for mechanical control between the controller and the supporting ring and which would require complex sealing provisions.

The optical imaging system may either be integrated as an eyepiece lens system into a visual endoscope or configured as an optical projecting system on principle. What is of particular interest, however, is the combination of a visual endoscope, the optical imaging system and a camera unit. In such a combination the casing element, which encloses the supporting ring, is detachably fastened on the camera unit in a watertight manner.

The controller has preferably an annular structure, or it is configured as a flat operating lever. It provided on its outside with a manipulating device for a radial or axial positional change of the controller, which is preferably adapted for operation by the operator's thumb. As the controller has a particularly suitable annular configuration it will also be referred to as control ring in the following.

As an alternative the positional shift of the supporting ring may also be implemented by means of coils generating a magnetic field, which are disposed in radial relationship with the control ring.

On account of the non-contacting transmission of forces between the control ring adapted for manipulation by an operator, on the one hand, and the supporting ring carrying the optical imaging system, on the other hand, it is possible to omit any sliding seals, sealing means and breakthroughs passing through the casing.

The following is an exemplary description of the present Invention, without any restricting of the general inventive idea, based on one embodiment, with reference to the annexed drawing wherein:

Figure 1:
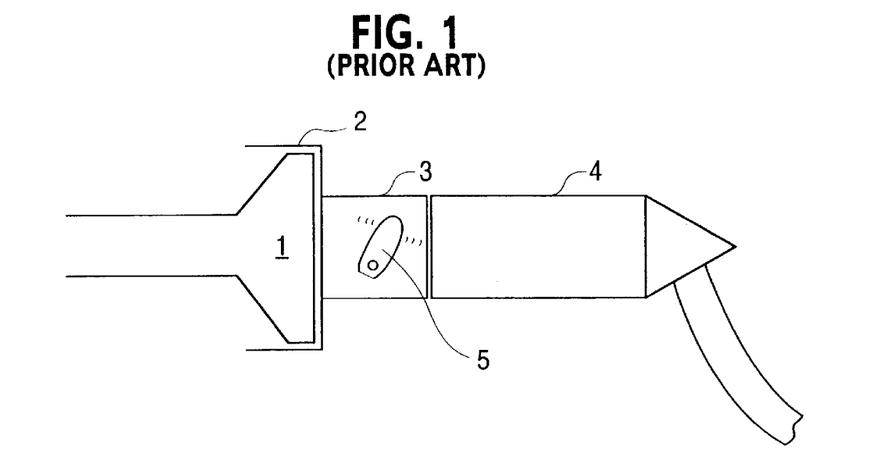
FIG. 1 is a schematic view of the link between a visual endoscope and a camera unit, Each of FIGS. 2a and FIG. 2b is a cross-sectional view taken through an embodiment presenting the inventive configuration.
Figure 2A:
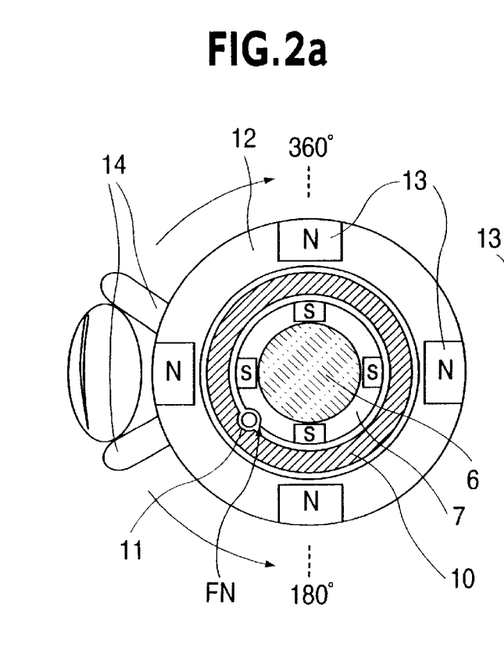
Figure 2B:
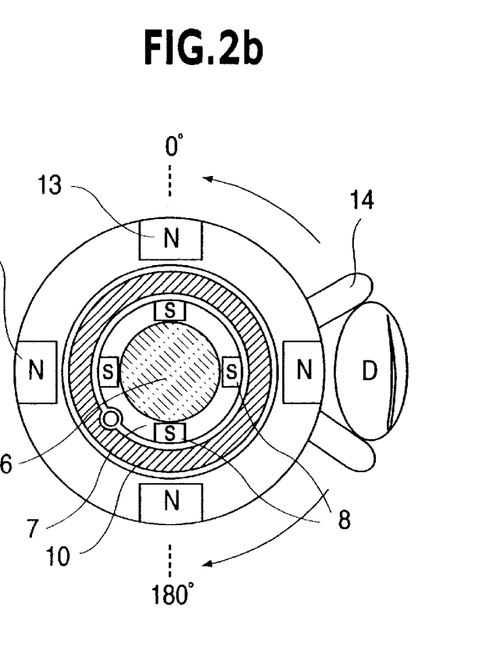

FIG. 1 is a view which serves to show clearly the fundamental structure of an endoscope video unit. A proximal eyepiece portion of a visual endoscope 1, which is schematically indicated, terminates in a coupler unit 2 on which the optical imaging system for sharply focusing the image for the joining video camera 4 is disposed. The optical imaging system is enclosed inside the casing 3 and is adapted for axial adjustment relative to the optical axis by means of exterior adjusting mechanisms 5. The disadvantages entailed by such a design have been discussed in the foregoing description. Each of FIGS. 2a and 2b is each a cross-sectional view taken through an inventive configuration of a device for changing the position of the optical imaging system. The optical imaging system is surrounded, at least partially, by an outside supporting ring 7 which includes, in this embodiment, four permanent magnets 8 which are equidistantly arranged on the supporting 7. An additional guiding groove FN is machined in the outer circumference of the supporting ring 7. This groove is more clearly evident from FIG. 3 which is a side view of the supporting ring together with the optical imaging system.

The supporting ring 7 is surrounded by a casing element 10 in an almost non-contacting manner, with the exception of the contact of the supporting ring 7 via a locating ball or a guiding pin 11. The distal side of the casing element 10 is securely connected, with appropriate sealing provisions, to the proximal end of the camera housing. The casing element 10 is sealed on its distal side with a glass panel. With this configuration, the casing element 10 ensures a watertight enclosure of the optical imaging system 6 provided inside. The only point of contact between the supporting ring 7 and the casing element 10 is the location of sliding engagement between the guiding pin or the locating ball 11 and the guiding groove FN inside the supporting ring, As the casing element 10 remains stationary with respect to the camera housing, a relative rotation of the supporting ring 7 can induce a change of the position of the optical imaging system 6 in a direction along the optical axis. The relative rotation of the supporting ring 7 is induced by a control ring 12 which surrounds the casing element 10 at least partially, with permanent magnets 13, which are larger than and are radially opposite, permanent magnets 8 in the supporting ring 7 in a number and are provided corresponding to the number of the permanent magnets 8. The larger size of the permanent magnets 13 is particularly expedient. Their magnet 8 fields interact with the radially opposite smaller magnets over a wider angular range and an axial range. A rotation of the control ring 12 relative to the casing element 10 causes a simultaneous rotation of the inner supporting ring 7 owing to the magnetic forces so that the inner supporting ring, guided via the guiding groove FN, undergoes a controlled change of its axial position.

The control ring 12 is preferably provided with manipulating means 14 on its outside, which consist of two bar elements in the embodiment illustrated here. These elements are adapted to the ergonomics of a user's thumb D and can be rotated by this thumb through 180°.

For an ergonomic operation of the control ring 12 for left-handed persons this ring is easily rotated in the range between 180° and 360°, as is illustrated in FIG. 2a, on account of the effective magnetic forces. At the same time however, a right-handed person is capable to operate the same manipulating means which is only rotated through 180° see FIG. 2b in this respect. In this manner one and the same means may be operated equally by left-handed and right-handed persons, without any necessity to disassemble the overall unit or to make other structural changes.

Figure 3:
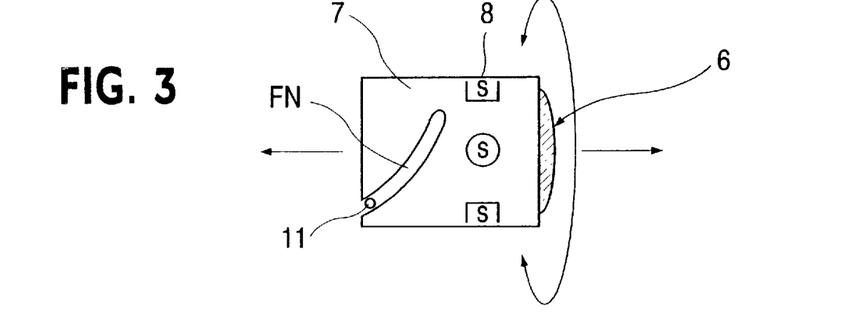
FIG. 3 illustrates a supporting ring with the optical imaging system, Each of FIGS. 4a and FIG. 4b is a schematic cross-sectional view usable for a clearer explanation of the adjusting mechanism.

FIG. 3 is a cross-sectional view of the supporting ring 7 together with the optical imaging system 6 and illustrates the guiding groove FN as well as the magnets 8 disposed on the outer circumference.

Figure 4A:
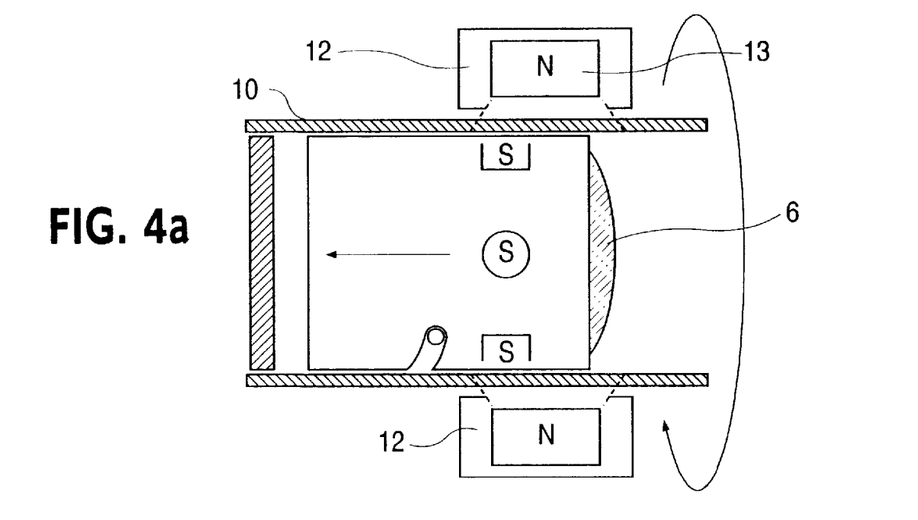
Figure 4B:
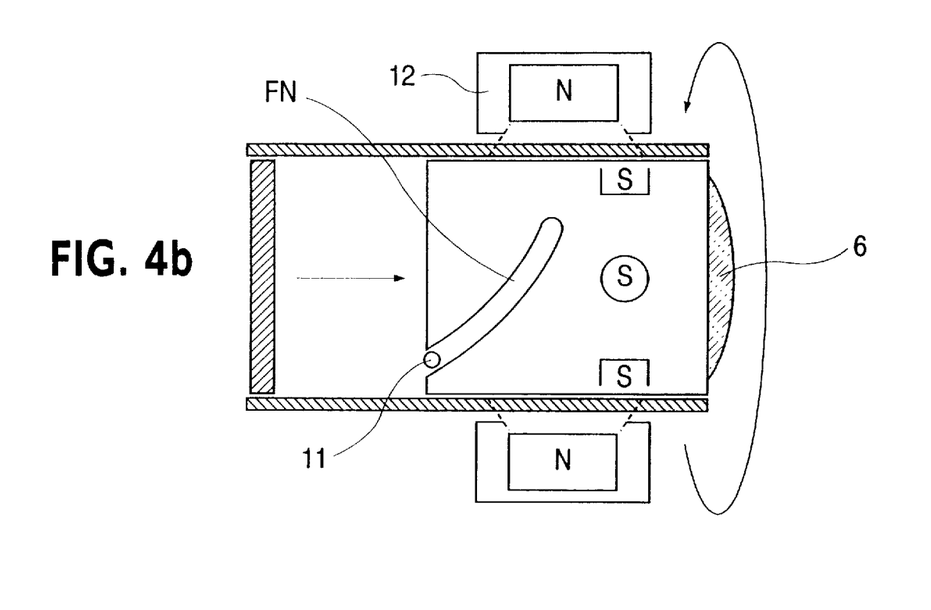

FIGS. 4a and 4b show the mechanism for axial displacement of the supporting ring 7 together with the optical imaging system 6 inside the casing element 10. As a result of a rotation of the control ring 12, the supporting ring 7 undergoes a rotating movement in the same direction, which is converted into an axial movement on account of the meshing engagement between the pilot pin or sphere 11, and the guiding groove FN. In the upper view in FIG. 4a the optical imaging system 6 is located in the rearmost left position whereas the optical imaging system 6 according to FIG. 4b is in the frontmost adjusting position. What is important is the aspect that the effective magnetic field generated by the magnets 13 inside the control ring 12 is so great that an interaction will be created between the magnets 13 and 8 all along the entire positional change. In this respect particular reference is made to the dotted lines in FIG. 4a and 4b, which symbolize the definition of the magnetic field and which represent at the same time also the range of axial movement of the magnets 8 within the supporting ring 7.

In the further figures, assemblies already described and identified by the same respective reference numerals are indicated in the drawing with the reference numerals so far used, without a repeated detailed description of these common assemblies. Another alternative embodiment consists in providing instead of the control ring configured as described above with the permanent magnets incorporated therein, this support as a rod-shaped magnet carrier which is mounted for axial displacement on the casing element 10 relative to the optical axis of the imaging system. With such a layout the guiding groove with a pilot pin may be omitted as the axial displacement of the rod-shaped magnet carrier made transmitted to the supporting ring directly.

Figure 5A:
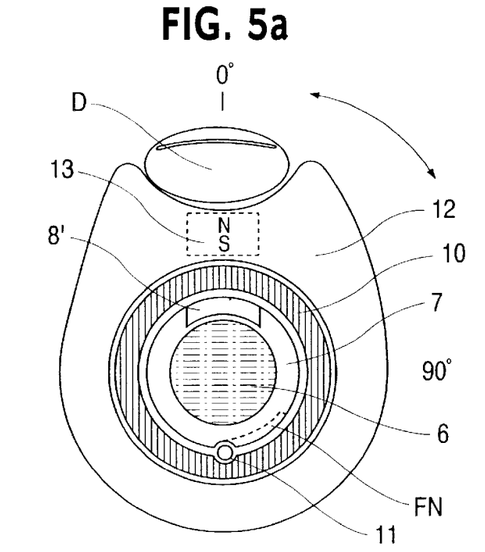
FIGS. 5a, and 5b show an embodiment provided with a single magnet in the control ring.

FIG. 5a is a cross-sectional view of an inventive embodiment, which is taken in a direction orthogonal on the optical axis of the imaging system 6. A single magnet 13 only is provided for axial displacement of the imaging system 6 which is connected to the supporting ring 7 which may include an iron core 8' as a unit sensitive to a magnetic field. The magneting effect of this single magnet influences the iron core 8' and any movement of the control ring 12, inclusive of the magnet 13, causes a direct tracking of the supporting ring 7 on account of the magnetic interaction between the magnet 13 and the iron core 8'.

Due to the current advances made in materials technology magnetic materials have become known which create such a strong magnetic field that a single magnet as shown in this embodiment is sufficient to induce an axial displacement of the optical imaging system 6 in parallel with the optical axis.

Figure 5B:
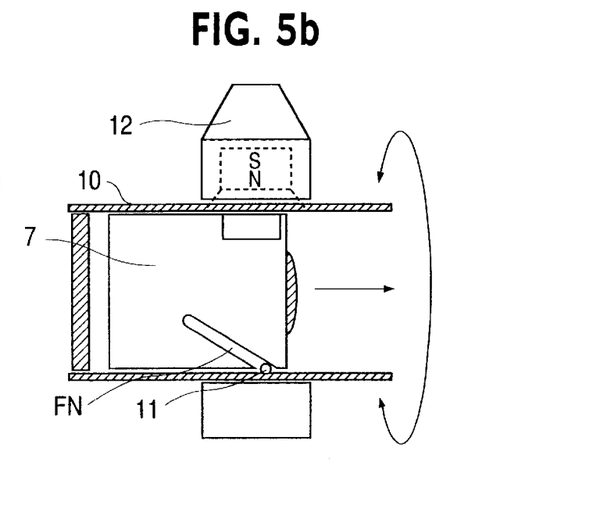

FIG. 5b shows a longitudinal sectional view of the same system. From this figure it is apparent that a single magnet 13 is provided in the control ring 12, which generates a magnetic field influencing the iron core 8'. On account of the radial rotation of the control ring 12 relative to the casing element 10, and due to the mechanical forced guidance ensured by the pilot pin 11 inside the guiding groove FN, the supporting ring 7 undergoes a rotation which displaces the supporting ring 7 axially relative to the optical axis of the imaging system 6.

Figure 6A:
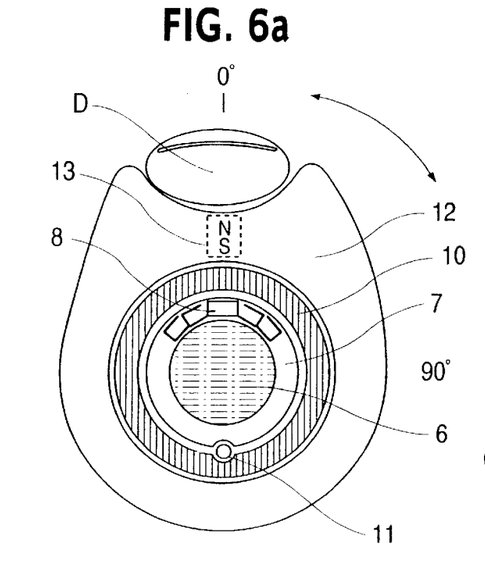
FIGS. 6a, and 6b illustrate an alternative of the embodiment according to FIG. 5.
Figure 6B:
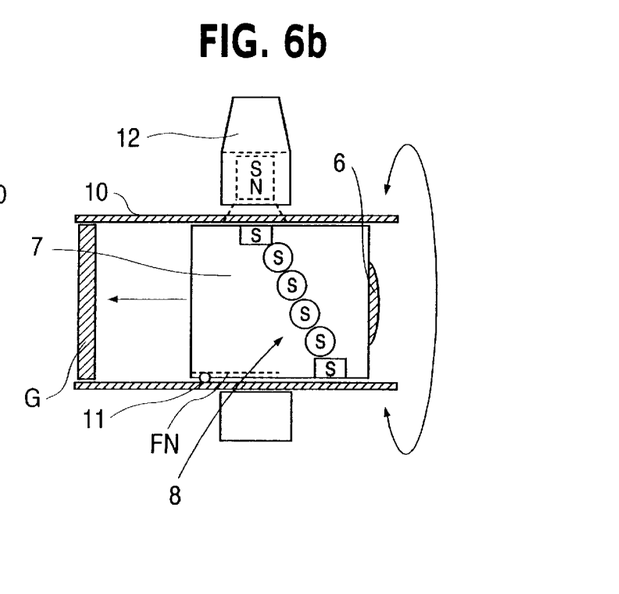

In distinction from the aforedescribed embodiment, a plurality of permanent magnets 8 is so disposed on the supporting ring 7 according to FIG. 6a that any rotation of the control ring 12 results directly in an axial displacement of the optical imaging system 6, without any necessity to provide for a forced guidance of the supporting ring 7 under control of the pilot pin 11 inside the guiding groove FN for an axial change of position. In the illustrated embodiment according to FIGS. 6a and 6b the guiding groove FN presents a linear configuration parallel with the optical axis. It is, however, also possible to use magnetic coil arrays, suitable for operation by means of appropriate electronic control circuits, instead of the permanent magnets 13 and 8 illustrated in the embodiments.

Figure 7:
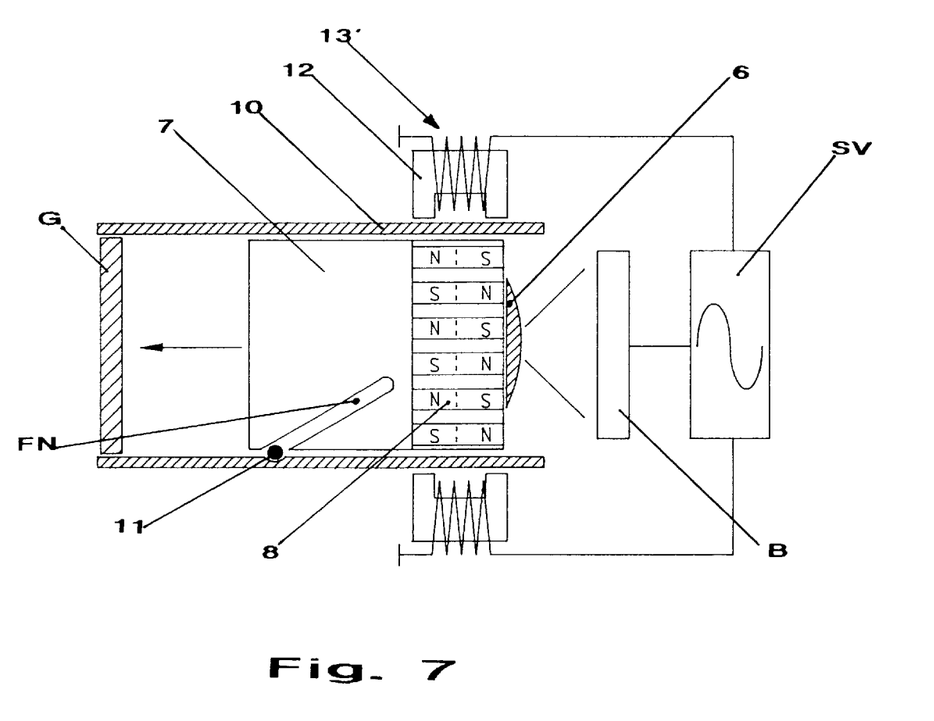
FIG. 7 is a view of an embodiment including a magnetizing coil in the control ring and a guiding groove in the supporting ring.

Another alternative embodiment for displacement of the supporting ring 7, however without the application of permanent magnets inside the control ring 12, is illustrated in FIG. 7. The control ring 12 is fastened with a magnetizing coil 13' on the casing element 10. With an appropriate power supply to the magnetizing coil 13', by means of a control amplifier SV, and with application of a suitable array of permanent magnets in the form of bar magnets 8 which are radially disposed around the supporting ring 7, it is possible to enforce rotation of the supporting ring 7, inclusive of the optical imaging system 6, by way of magnetic interaction, with the result that, due to the forced guidance of the pilot pin 11 in the guiding groove FN, the supporting ring 7 induces an axial displacement of the optical imaging system 6. Just for the sake of completion it should be noted that the casing element 10 is closed on one side by a glass panel G. An image sensor B, which is connected to the control amplifier SV, is located directly opposite to the optical imaging system 6.

Figure 8:
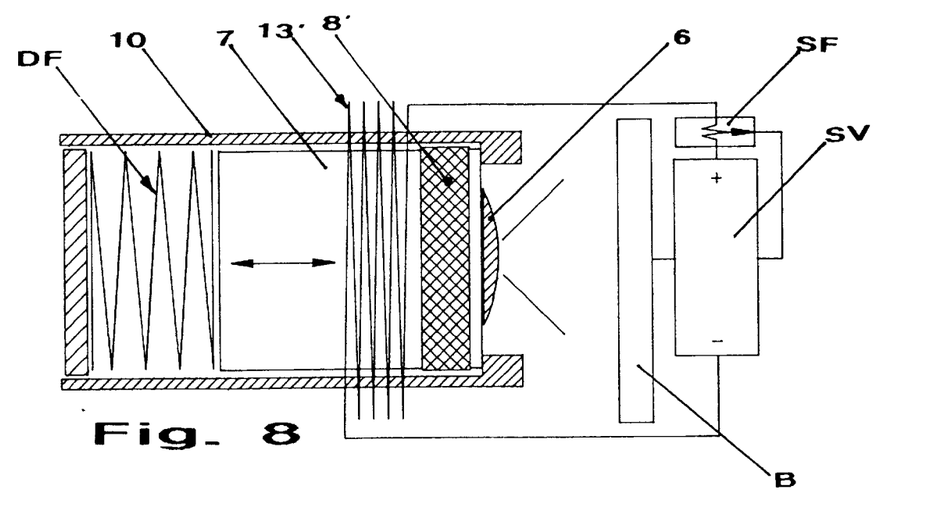
FIG. 8 shows an embodiment provided with a magnetizing coil in the control ring as well as with a compression spring.
Figure 9:
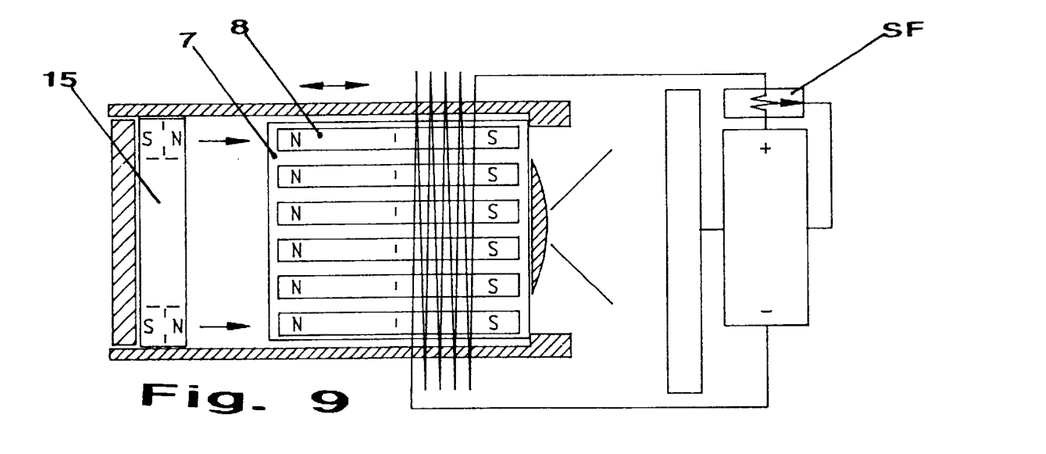
FIG. 9 is a view of the embodiment as in FIG. 8, however without a compression spring, but with an additional magnetic ring.
Figure 10:
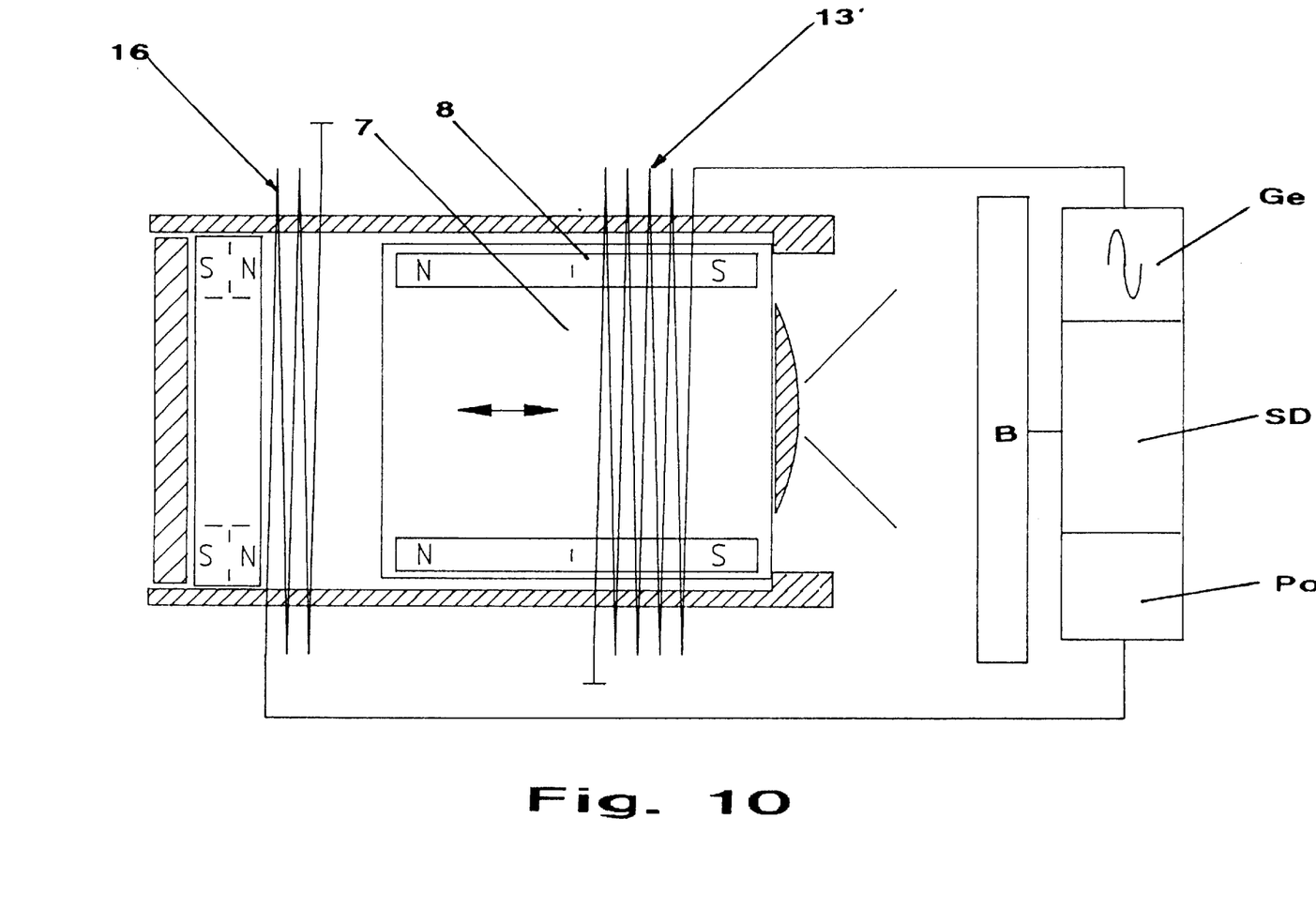
FIG. 10 shows an embodiment with an autofocusing coil.

FIG. 8 illustrates an improved configuration of the aforedescribed embodiment according to FIG. 7, wherein a forced guidance of the supporting ring 7 by means of a pilot pin and a guiding groove is omitted. There the supporting ring 7, inclusive of the optical imaging system 6, is biased into a specified initial position by means of a compression spring DF. Merely an iron ring 8' is mounted on the supporting ring 7. By means of an inductive magnetizing coil 13', which is connected to a control amplifier SV via a current detector SF and hence is supplied with electric current, it is possible to use the magnetic interaction between the magnetic field of the inductive magnetizing coil 13' and the magnetizable iron ring 8', with appropriate power supply to the coil, in order to generate an appropriate force acting upon the supporting ring 7, e.g. in opposition to the resilient force produced by the compression spring DF, with the result that a controllable displacement of the optical imaging system 6 is now possible in parallel with the optical axis. If an appropriate current detector SF is used, it is moreover possible to detect the precise position of the magnetizable iron ring 8' relative to the inductive magnetizing coil 13', which is fastened on the casing element 10, so that an autofocusing function of the optical imaging system 6 will be achievable with suitable control based on the information received from the image sensor B. In accordance with the embodiment illustrated in FIG. 9 a magnetic ring 15 may be used, instead of the compression spring DF. The magnetic polarization as ring 15 is so oriented that the magnetic poles of a plurality of permanent bar magnets 8, which are radially disposed in the supporting ring 7, are in homopolar opposition. In all other respects, the structure corresponds to the embodiment according to FIG. 8 and equally permits the detection of the position of the optical imaging system by means of a separate current detector SF. The embodiment according to FIG. 10 represents an extended improvement of the aforedescribed embodiment according to FIG. 9 and is provided with a specific sensor coil 16 for detecting the position of the optical imaging system relative to the optical axis. Sensor coil 16 is preferably operated in an active 100 Hz mode, with the voltage amplitude being influenced by the inductive effect produced by the permanent magnet 8 which is provided, e.g. in the form of a bar magnet on the supporting ring 7, and is used as a measurand. In all other respects, the structure of this embodiment corresponds to the aforedescribed embodiments. An additional generator Ge, heterodyned with DC voltage, is provided for driving the operating coil 13'. Generator GE operates preferably on 100 Hz. An additional focusing detector SD filters high frequency out of the video signal which is obtained by means of the image sensor B. The sharpness of the video signal is to be determined as a function of the high-frequency edges. The sensor coil 16 is additionally controlled by a position detector Po.

The omission of any sealing provisions, which are required the prior art, e.g. in the form of sliding seals, results in a particularly smoothly moving non-wearing and simple structure for changing the position of optical imaging systems. Any common bores for a mechanical control may be dispensed with. As the casing element, which is made of an anti-magnetic metal or plastic or ceramic material, is preferably covered on one side by a glass panel and is connected, on the other side, via a sealed thread section to the camera unit for watertight enclosure of the optical imaging system therein, the device presenting the inventive configuration complies with any current requirements in terms of sterilization in biomedical engineering.

I claim:

1. A device for changing the position of an optical imaging system, comprising:
   a supporting ring for surrounding the optical imaging system at least partially, said supporting including at least one unit which generates or is sensitive to a magnetic field,
   a casing element surrounding said supporting ring in a largely non-contacting manner, to provide a watertight enclosure of said supporting ring, inclusive of the optical imaging system, and
   a controller surrounding said casing element at least partially, said controller including at least one unit generating or sensitive to a magnetic field in a radial or axial direction relative to said unit in said supporting ring which generates or is sensitive to a magnetic field, said controller unit causing non-contacting displacement of said supporting ring, inclusive of the optical imaging system, along the direction of the imaging system optical axis without any wear-inducing engaging operative mechanisms, by means of a magnetic force.

2. A device according to claim 1, further comprising manipulating means, having an annular configuration or the shape of a planar lever, on the outside of said controller for causing a radial and/or axial change of the position of said controller, operation of said manipulating means causing an axial change of position of said supporting ring.

3. A device according to claim 1, wherein said supporting ring includes four units generating or sensitive to a magnetic field, equidistantly arranged therearound; and said controller includes a further four units generating or sensitive to a magnetic field, equidistant therearound.

4. A device according to claim 1, wherein said unit in said controller generating or sensitive to a magnetic field is a permanent magnet in the form of a bar magnet or a hollow cylinder.

5. A device according to claim 1, wherein the angular and axial extents of said at least one unit in said controller which generates or is sensitive to a magnetic field are larger than the angular and axial extents of said at least one unit in said supporting ring which generates or is sensitive to a magnetic field.

6. A device according to claim 1, wherein the radially outwardly oriented magnetic polarization of said at least one unit in said supporting ring which generates or is sensitive to a magnetic field is inverted relative to the radially inwardly oriented magnetic polarization of said at least one unit in said controller which generates or is sensitive to a magnetic field.

7. A device according to claim 1, wherein said controller is rotatable through 360° around said casing element.

8. device according to claim 2, wherein said manipulating means comprises two projecting bar elements between which an operator can place his or her thumb for rotating said controller with a single hand to the left or to the right.

9. A device according to claim 1, wherein said manipulating means on said controller has a contour ergonomically adapted to a thumb for single-handed displacement of said controller in parallel with the optical axis of the optical imaging system.

10. A device according to claim 1, wherein said controller is adjustable in two positions for operation by either a left-handed operator or a right-handed operator.

11. A device according to claim 1, wherein said supporting ring has a guiding groove therein, and said casing element has a guiding element on the inside thereof for sliding engagement in the guiding groove.

12. A device according to claim 11, wherein the guiding groove slopes so that rotation of said controller within a range of 180° permits travel all through the range of positional change of said optical imaging system.

13. A device according to claim 1, wherein said controller is displaceable in a direction parallel to the optical axis of the optical imaging system.

14. A device according to claim 1, wherein said at least one unit generating a magnetic field in said controller comprises at least one electrically controllable coil.

15. A device according to claim 1, wherein said controller comprises an electrically controllable coil.

16. A device according to claim 1, further comprising an induction coil and a measuring circuit for detecting the position of said supporting ring and the optical imaging system.

17. A device according to claim 16, further comprising a magnetic ring coaxially spaced from said supporting ring and having a magnetic polarization so oriented that homopolar magnetic poles between said magnetic ring and said supporting ring on at least one unit generating or sensitive to a magnetic field are opposed to each other.

18. A device according to claim 1, further comprising a spring element for biasing said supporting ring in a direction parallel with the optical axis of the imaging system.

19. A device according to claim 1, wherein said casing element has a window sealing at least one side thereof.

20. A device according to claim 1, wherein said device is adapted to mount the optical imaging system between an object and said camera unit.

21. A device according to claim 20, wherein the object is a visual endoscope or an object to be imaged.

22. A device according to claim 1, wherein said device is adapted to mount the optical imaging system between a visual endoscope and a camera unit.

23. A device according to claim 22, wherein said casing element is adapted for detachable watertight attachment on the camera unit.

* * * * *